US011696593B2

(12) United States Patent
Dimitrelos et al.

(10) Patent No.: US 11,696,593 B2
(45) Date of Patent: Jul. 11, 2023

(54) ASTAXANTHIN NUTRITIONAL COMPOSITIONS AND USES

(71) Applicant: Bioscience Formulators, LLC, Boca Raton, FL (US)

(72) Inventors: Geronimos Dimitrelos, Plantation, FL (US); Raphael Dominguez, Fort Lauderdale, FL (US)

(73) Assignee: Bioscience Formulators, LLC, Boca Raton, FL (US)

( * ) Notice: Subject to any disclaimer, the term of this patent is extended or adjusted under 35 U.S.C. 154(b) by 893 days.

(21) Appl. No.: 16/549,778

(22) Filed: Aug. 23, 2019

(65) Prior Publication Data

US 2020/0060322 A1 Feb. 27, 2020

Related U.S. Application Data

(60) Provisional application No. 62/722,465, filed on Aug. 24, 2018.

(51) Int. Cl.
*A23L 33/12* (2016.01)
*A61K 31/122* (2006.01)
*A61K 36/18* (2006.01)
*A61K 31/66* (2006.01)
*A61K 31/19* (2006.01)

(52) U.S. Cl.
CPC ............ *A23L 33/12* (2016.08); *A61K 31/122* (2013.01); *A61K 31/19* (2013.01); *A61K 31/66* (2013.01); *A61K 36/18* (2013.01)

(58) Field of Classification Search
CPC ........ A23L 33/15; A23L 33/12; A23L 33/105; A61K 2300/00; A61K 31/122; A61K 31/19; A61K 31/66; A61K 36/18; A61K 36/185; A61K 36/53
See application file for complete search history.

(56) References Cited

U.S. PATENT DOCUMENTS

| | | |
|---|---|---|
| 6,248,390 B1 | 6/2001 | Stillman |
| 6,265,450 B1 | 7/2001 | Asami et al. |
| 6,277,417 B1 | 8/2001 | Anderson |
| 7,320,797 B2 | 1/2008 | Gupta |
| 7,589,057 B2 | 9/2009 | Chang et al. |
| 8,193,376 B2 | 6/2012 | Gupta |
| 8,349,376 B1 | 1/2013 | Bezzek |
| 8,592,662 B2 | 11/2013 | Todd, Jr. et al. |
| 8,697,138 B2 | 4/2014 | Bruheim et al. |
| 9,233,081 B2 | 1/2016 | Oda et al. |
| 9,295,698 B2 | 3/2016 | Minatelli et al. |
| 9,320,759 B2 | 4/2016 | Pan |
| 9,763,897 B2 | 9/2017 | Minatelli et al. |
| 2004/0234587 A1* | 11/2004 | Sampalis ................ A23L 33/30 514/27 |
| 2009/0169682 A1 | 7/2009 | Okumura et al. |
| 2013/0059768 A1 | 3/2013 | Hallaraker et al. |
| 2014/0248369 A1 | 9/2014 | Minatelli et al. |
| 2015/0182475 A1* | 7/2015 | Minatelli ............. A61K 35/612 514/691 |
| 2015/0231192 A1 | 8/2015 | Minatelli et al. |
| 2016/0081975 A1* | 3/2016 | Bromley ................ A61K 31/12 514/168 |

FOREIGN PATENT DOCUMENTS

| | | |
|---|---|---|
| CN | 101313897 A | 12/2008 |
| CN | 102935116 A | 2/2013 |
| CN | 103599137 A | 2/2014 |
| CN | 103816212 A | 5/2014 |
| CN | 104877882 A | 9/2015 |
| CN | 104893927 A | 9/2015 |
| CN | 104893932 A | 9/2015 |
| CN | 104922299 A | 9/2015 |
| CN | 104984102 A | 10/2015 |
| CN | 105031315 A | 11/2015 |
| CN | 105106184 A | 12/2015 |
| CN | 105106185 A | 12/2015 |
| CN | 105250247 A | 1/2016 |
| CN | 105250248 A | 1/2016 |
| CN | 105535930 A | 5/2016 |
| CN | 105560838 A | 5/2016 |
| CN | 106038612 A | 10/2016 |
| CN | 106729675 A | 5/2017 |
| CN | 107048104 A | 8/2017 |
| CN | 107080769 A | 8/2017 |
| CN | 107260801 A | 10/2017 |
| CN | 107307403 A | 11/2017 |
| CN | 107468677 A | 12/2017 |
| CN | 107625758 A | 1/2018 |
| JP | 2002226368 A | 8/2002 |
| JP | 2006008713 A | 1/2006 |
| JP | 2006008715 A | 1/2006 |

(Continued)

OTHER PUBLICATIONS

Xymogen (Xymogen, Product Catalog, 2017). (Year: 2017).*
ScienceBasedHealth (Year: 2011).*

*Primary Examiner* — Umamaheswari Ramachandran
(74) *Attorney, Agent, or Firm* — Harness, Dickey & Pierce, P.L.C.

(57) ABSTRACT

Nutritional compositions (e.g., dietary supplements or nutraceutical compositions) comprising astaxanthin and, in various embodiments, a second nutritional component selected from the group consisting of phospholipids, omega-3-acids, omega-5-fatty acids, omega-6-fatty acids, omega-7-fatty acids, omega-9-fatty acids, vitamin E compounds, and mixtures thereof. For example, the nutritional compositions may contain astaxanthin along with components such as omega-3 fatty acids, phospholipids comprising a major amount of phosphatidyl choline and phosphatidyl inositol, and vitamin E comprising a major amount of delta-tocotrienol. Methods of improving the nutritional status of subject include administering the nutritional compositions, and may provide health benefits, such as reducing A1C blood levels.

20 Claims, No Drawings

(56) References Cited

FOREIGN PATENT DOCUMENTS

| | | |
|---|---|---|
| JP | 2007126455 A | 5/2007 |
| JP | 2007153846 A | 6/2007 |
| JP | 2008106029 A | 5/2008 |
| JP | 2009007346 A | 1/2009 |
| JP | 2009215184 A | 9/2009 |
| JP | 2009269832 A | 11/2009 |
| JP | 2011173850 A | 9/2011 |
| WO | 07046083 A2 | 4/2007 |
| WO | 09048120 A1 | 4/2009 |

* cited by examiner

ASTAXANTHIN NUTRITIONAL COMPOSITIONS AND USES

CROSS-REFERENCE TO RELATED APPLICATIONS

This application claims the benefit of U.S. Provisional Application No. 62/722,465, filed on Aug. 24, 2018. The entire disclosure of the above application is incorporated herein by reference.

BACKGROUND

The present technology relates to nutritional compositions and methods. In various embodiments, such compositions and methods include astaxanthin and one or other nutritional substances.

The nutritional art discloses a wide variety of nutritional supplements that may provide benefits, such as symptom relief, to humans or other subjects having physiological diseases or disorders. Such supplements include "nutraceuticals," which may offer physiological benefits similar to pharmaceuticals, but are regulated as dietary supplements or food additives by the governmental health agencies, such as the U.S. Food & Drug Administration in the United States. For example, such nutritional supplements may have antioxidant properties, which may be associated with the amelioration of symptoms of disorders associated with inflammation.

Nutritional supplements containing astaxanthin are known in the art. Astaxanthin is a carotenoid found predominantly in marine life. For example, astaxanthin is produced by algae such as *H. pluvialis*, and is the source of the red color of a variety of other organisms such as krill, fish, and shrimp, and lobsters.

While compositions containing astaxanthin are known, the benefits are not fully appreciated. Moreover, there is a need to produce improved compositions comprising astaxanthin and other nutritional compounds for use in maintaining general health and in treating or ameliorating symptoms associated with physiological diseases and disorders.

SUMMARY

The present technology provides nutritional compositions (e.g., dietary supplements or nutraceutical compositions) comprising astaxanthin and, in various embodiments, a second nutritional component selected from the group consisting of phospholipids, omega-3-acids, omega-5-fatty acids, omega-6-fatty acids, omega-7-fatty acids, omega-9-fatty acids, vitamin E compounds, and mixtures thereof. In various aspects such nutritional compositions contain astaxanthin along with other synergistic components. Such components include omega-3 fatty acids, phospholipids comprising a major amount of phosphatidyl choline and phosphatidyl inositol, and vitamin E comprising a major amount of delta-tocotrienol. In exemplary fashion, the composition consists of 1-5 parts astaxanthin, 150-500 parts of omega-3 fatty acids, 10-40 parts of delta-tocotrienol, and 30-150 parts phospholipids. (Note, the parts reflect the relative weight proportion of the four components; as such they do not necessarily add up to one hundred parts.) When the parts of the four components are considered as milligrams, the four components can be used as part of a daily dose that delivers 1 to 5 mg of astaxanthin. Such a composition would contain 1-5 mg astaxanthin, 150-500 mg of omega-3 fatty acids, 10-40 mg delta-tocotrienol, and 30-150 mg phospholipids, as a non-limiting example.

For example, the present technology provides a unit dose composition (e.g., for consumption by a subject in a single dose) comprising:
 from 1 to 5 (e.g., 2) mg astaxanthin;
 from 200 to 300 (e.g., 250) mg total omega-3 acids;
 from 70 to 80 (e.g., 75 mg) phospholipids;
 from 0.5 to 1 (e.g., 0.8) mg total omega-6 fatty acids;
 from 10 to 20 (e.g., 15) mg total omega-5 and omega-7 fatty acids;
 from 12 to 16 (e.g., 14.5) mg total omega-9 fatty acids; and
 from 15 to 25 (e.g., 20 mg) vitamin E compounds comprising more than 80%, preferably more than 90%, by weight of delta-tocotrienol and less than 10%, preferably less than 5%, of alpha-tocopherol.

The composition may be formulated into any suitable dosage form, such as a softgel. In some embodiments the composition may be formulated into a food or beverage.

In various embodiments, the composition further comprises one or more of rosemary extract, coconut oil, D-limonene, algal oil, moringa seed oil, Sea Buckthorn pulp oil, and pomegranate seed oil. In some embodiments, the daily dose contains all of rosemary extract, coconut oil, D-limonene, algal oil, moringa seed oil, Sea Buckthorn pulp oil, and pomegranate seed oil. In some embodiments the astaxanthin is from Haemotococcus pluvialis algae, the omega-3 fatty acids are from algal oil and comprise a major amount of docosahexaenoic acid and eicosapentaenoic acid, the lecithin is from sunflowers, and the vitamin E is from annatto.

In some embodiments, the unit dose has no beta-carotene and no Coenzyme Q10. In these or other embodiments, the dose has no citric acid and no phosphoric acid. In still other of these or other embodiments, the daily dose has essentially no alpha-tocopherol.

The present technology also provides methods for improving the nutritional status of a human or other animal subject, comprising administering (i.e. consumption by the subject of) a composition of the present technology. Such methods include administration of nutritional materials comprising:
 from 2 to 6 (e.g, 4) mg astaxanthin;
 from 400 to 600 (e.g., 500) mg total omega-3 acids, for example containing about 300 mg of DHA and about 150 mg of EPA;
 from 100 to 200 (e.g., 150) mg phospholipids;
 from 1 to 3 (e.g., 1.6) mg total omega-6 fatty acids;
 from 25 to 35 (e.g., 30) mg total omega-5 and omega-7 fatty acids;
 from 25 to 35 (e.g., 29) mg total omega-9 fatty acids; and
 from 35 to 45 (e.g., 40) mg vitamin E compounds comprising more than 90% by weight of delta-tocotrienol and less than 5% by weight of alpha-tocopherol.
In various embodiments, administering comprises ingestion by the subject of two unit dosage forms comprising the nutritional materials.

In various embodiments, the compositions and methods described herein provide empirically observed physiological effects, even though the FDA has not reviewed any claims of treatments, and the compositions are not intended to diagnose or treat any disease. In various examples, a method of reducing A1C in a subject, or of improving renal function in a subject, or of improving cognitive function in a subject, comprises administering to the patient any of the daily doses or formulations set forth herein, such as tablets, capsules, softgels, beverages, or food products.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

Compositions

The present technology provides compositions comprising certain nutritional substances, including astaxanthin, in a carrier suitable for oral administration to a human or other animal subject. In various aspects, such compositions are dietary supplements, nutraceutical compositions, or pharmaceutical compositions. As discussed further below, preferred compositions include nutraceutical compositions useful for improving the nutritional state of subjects having a physiological disorder or disease, and may ameliorate symptoms associated with such conditions.

In various embodiments, the compositions described herein contain a mixture of "active" components selected from the group consisting of astaxanthin, omega-3 fatty acids, a vitamin E component as further defined herein, phospholipids, and mixtures thereof. Preferably, the compositions comprise all four active components. In various embodiments, the compositions further comprise omega-n fatty acids.

Astaxanthin

Astaxanthin is a lipid-soluble keto-carotenoid, having the IUPAC name of 3,3'-dihydroxy-β-carotene-4,4'-dione, and Chemical Abstracts Registry® Number 472-61-7. It has a characteristic orange red color due to an extended chain of conjugated double bonds. It is produced naturally by algae, and may be produced synthetically as a mixture of stereoisomers. Krill are also a source of astaxanthin because they have eaten phytoplankton that have fed on the algae. Natural astaxanthin found in krill and algae is the (3S, 3'S) isomer. Because the naturally occurring stereoisomer is preferred and because the yield of astaxanthin is high, a preferred source of astaxanthin is the alga *Haematococcus pluvialis*, which produces an algal oil containing astaxanthin as a major component along with omega-3 acids and other components. Such algae may be produced using the methods described in U.S. Pat. No. 9,243,219, Dimitrelos, issued Jan. 26, 2016, and US Patent Application Publication 2019/0225931, Dimitrelos, published Jul. 25, 2019, both of which are incorporated by reference herein.

Omega-3 Fatty Acids

Omega-3 fatty acids are polyunsaturated fatty acids with a carboxyl group (COOH) at the first, or alpha end, and a methyl at the end of the fatty acid chain, called the omega end. In omega-3 fatty acids, there is a double bond between the $3^{rd}$ and $4^{th}$ carbons from the omega end. The two most common omega-3 fatty acids are eicosapentaenoic acid (EPA) and docosahexaenoic acid (DHA). They are found together in hill oil or algal oil, and are also commercially available as a pure synthetic version. In various embodiments the omega-3 fatty acids are obtained from algal oil.

Omega-n Fatty Acids

Other unsaturated fatty acids are designated generally as omega-n, meaning that there is a double bond between the carbon atoms numbered n and n+1 from the omega end of the chain. These are available from commercial sources, and can be obtained as a minor component of oils produced by krill and algae. Examples include omega-4, omega-5, omega-6, omega-7, omega-8, and omega-9 fatty acids. To illustrate, oleic acid is an omega-9 fatty acid. In various embodiments the omega-n fatty acids are obtained from algal oil.

Vitamin E Component

The compositions of the present technology also contain vitamin E components or compounds. As used herein, the vitamin E family has four members referred to as tocotrienols (alpha, beta, gamma, delta) and four called tocopherols (alpha, beta, gamma, delta). One difference is that tocotrienols have an unsaturated chain, while tocopherols have a saturated chain. Chemically, they all act as antioxidants, but alpha-tocopherol has the highest biological activity and is the isomer preferentially absorbed in humans. As further described below, the compositions of the present technology in various embodiments comprise a vitamin E component that acts synergistically with the other actives.

In preferred embodiments, the vitamin E component is selected to contain a major amount of delta-tocotrienol and a minor amount of alpha-tocopherol. For example, the vitamin E component can contain 10% or less by weight alpha-tocopherol. In other embodiments, the vitamin E component is less than 10%, less than 5%, less than 2%, less than 1%, less than 0.5%, or less than 0.1% alpha-tocopherol, or else the alpha-tocopherol is essentially 0%, being essentially undetectable in the composition. Meanwhile, the vitamin component is greater than 80%, greater than 90%, greater than 95%, greater than 98%, or greater than 99% delta-tocotrienol. In this way the use of the dominant vitamin E component is minimized or eliminated in favor of a certain tocotrienol. Delta-tocotrienol is commercially available and is conveniently derived from annatto, a vitamin E source naturally high in delta-tocotrienol.

Phospholipids

The present compositions also contain phospholipids. Preferred phospholipids include those rich in phosphatidyl inositol and phosphatidyl choline, such as those phospholipids derived from sunflower lecithin.

Optional Components

Compositions of the present technology may contain additional nutritional materials. Such optional nutritional materials include seed oils (e.g., moringa seed oil, pomegranate seed oil, sea buckthorn pulp oil), rosemary oil, coconut oil, D-limonene, eucalyptus oil, and mixtures thereof.

Formulations

The compositions may comprise the active materials and optional materials described above along with other components that serve as a carrier for the actives. The carrier contains various oils and other ingredients as further described.

Compositions may be provided in any dosage form, preferably for oral administration to, or consumption by, a human or other animal. For example, suitable dosage forms include tablets, sachets, capsules, and liquids. In some embodiments, the compositions are contained in capsule or softgel dosage forms. In some embodiments, softgels comprise one or more of gelatin, carrageenan or similar materials with plasticizers such as glycerin or sorbitol. In some embodiments, such capsules are vegan, comprising tapioca, glycerin, sorbitol, and water. Dosage forms may also contain flavorants and colorants.

In some embodiments, compositions described herein are incorporated into a food that contains an oil component, with little modification of the manufacturing procedure. Examples include, without limitation, olive oil, condiments, sauces, dressings, prepared foods, cereals, snacks, protein bars and powders, children's food, and so on, including animal feeds.

Beverages can be formulated using a liposomal method or comparable technique to make the hydrophobic active ingredients soluble in oil or water, as the case may be. Liposomal technologies useful herein include those known in the art, generally comprising trapping materials in a microscopic sphere made up of a layered membrane consisting of phospholipid molecules. This phospholipid membrane protects the enclosed materials, so as to effectively deliver the materials to cells in the body.

In some aspects, formulating the compositions of the present technology can be conceived as combining a first active composition—e.g., one consisting of the four actives—with a second composition containing all the other components such as the noted oils and the like. The amount of actives in the final dose is determined by how much of the first active composition is used, and by the relative amounts of the four actives there are in the actives composition. The relative amounts of the four actives can be expressed either in parts by weight or in percent by weight.

In various embodiments, the compositions of the present technology comprise nutritionally-effective levels of the active materials. Such levels are sufficient to provide a beneficial physiological effect without significant adverse effects, considering such factors as the specific active materials used in the compositions, the nature and level of other materials contained in the compositions, the intended use of the composition, and the intended dosage regimen for the composition.

In various embodiments, compositions are provided comprising synergistic levels of the active materials. Without limiting the scope or utility of the present technology, compositions comprising two or more materials at synergistic levels provide nutritional benefits, such as in improving nutritional status or amelioration of symptoms, greater than the nutritional benefits of a composition comprising each such material by itself. For example, in some aspects, it is believed that astaxanthin at a daily dose of about 1 to 12 mg/day is providing the main activity, while the other actives are providing synergistic improvements in combination with the astaxanthin. With the discovery of the combination of four synergistic active ingredients, the relative amounts can be varied to provide compositions with desirable properties.

To illustrate, in an embodiment the composition contains 1-5 parts astaxanthin, 150-500 parts omega-3 acids, 10-40 parts vitamin E, and 30-150 parts phospholipids, where parts are parts by weight. Here the parts do not necessarily add to one hundred. A dose delivering a desired amount of astaxanthin can be formulated from such a composition, no matter what other non-active materials are in the composition. The designation in parts by weight establishes the relative amount of the 4 active materials.

The relative amounts of the actives can also be expressed as percent by weight, based on the four actives adding to 100%. Thus in another illustration (not equivalent to the example in the previous paragraph), the composition contains active ingredients and carrier components, wherein the active ingredients are 0.1-10% astaxanthin, 10-90% omega-3 acids, 0.1-50% vitamin E, and 1-60% phospholipids, where the percentages are by weight and add up to 100%. Again, a dose delivering a desired amount of astaxanthin (or of any other active) can be readily calculated from this information.

In general, the active materials of the doses, compositions, supplements, and formulations are 0.1-99.7 wt. % astaxanthin; 0.1-99.7 wt. % omega-3 acids; 0.1-99.7 wt. % vitamin E and 0.1-99.7 wt. % phospholipids, where the percentages are based on the total weight of the active materials and the total weights add up to 100%. This provides for a wide range of active compositions, for example where three components are present at 0.1% and one is at 99.7%, or where the four are equal at 25 wt. % each, in non-limiting fashion. It is also intended to disclose the sub-ranges discussed above that a skilled person in the art would recognize. Active materials in such ranges are formulated with optional carrier materials described herein.

In various embodiments, compositions of the present technology do not contain (i.e., at significant levels) certain nutritional substances, and may consist essentially of or consist of the active materials described above. Thus, in various embodiments the compositions are characterized as lacking one, two, three, or all four of or more of coenzyme Q10, beta-carotene, citric acid, and phosphoric acid. For example, in certain embodiments, the compositions do not contain carotenoid molecules other than astaxanthin. In some embodiments, the compositions do not contain beta-carotene, lutein, zeaxanthin, echinenone, canthaxanthin, coenzyme Q10 or phosphoric acid, individually or in combination. Without limiting the scope or utility of the present technology, it is believed that absence of one or more of such components that are present in compositions of the prior art leads at least in part to an observed efficiency and synergy of action of the compositions of the present technology.

Nutritional Methods

The present technology also provides nutritional methods comprising administering a nutritionally-effective amount of composition of the present technology to a human or other animal subject. By "administering," it is understood that compositions may be provided to a subject for consumption by the subject, or directly administered to the subject. In various embodiments, methods comprise administering one or more unit doses of the compositions of the present technology described above. For example, methods may comprise administering a daily dose of 1 to 12 mg astaxanthin per day, provided 1 to 4, and preferably in 1 to 2 unit dose compositions (e.g., gel capsules).

In various embodiments, the present technology provides methods for improving the nutritional status of the subject. It is understood that "nutritional status" includes any condition associated with the administration of the active materials and other components of the compositions of the present technology as nutritional materials, and any nutritional, cosmetic, physiological, psychological or other benefits that may associated with such materials and components. The present methods include such uses as may be appreciated by one of ordinary skill in the art based on the prior art and the present disclosure according to sound medical or nutritional practice. In various embodiments, such methods include methods that are subject to regulation by the U.S. Food & Drug Administration or other governmental authorities regulating the labeling or other marketing of pharmaceutical, nutraceutical, nutritional supplement, or food products, including health claims, nutrient content claims, and structure/function claims. In various embodiments, compositions of the present technology may be used as pharmaceuticals, nutraceuticals, functional foods, dietary supplements, or food compositions, subject to appropriate regulatory requirements and approvals. To be clear, the present disclosure that certain compositions of the present technology may be used in some methods having a certain regulatory status (e.g., use as a pharmaceutical for the treatment of a disease or disorder) does not mean that those or other compositions of the present technology are only intended for such use or necessarily have that regulatory status, such that the compositions may be used for other methods having a different regulatory status (e.g., as nutritional supplements).

In some embodiments, compositions of the present technology may have a variety of modes of action, contributing to the overall advantages of providing effective levels of the astaxanthin in synergistic mixture. In various embodiments, ingestion or administration of astaxanthin in the synergistic mixture disclosed herein have been observed to reduce inflammation, improve intestinal flora, inhibit neovascularization, inhibit metalloproteinases, promote the immune system, reduce oxidative DNA damage, lower the effects of COX inhibitors, suppress Th1 while stimulating Th2, inhibit the activity of 5-α-reductase, increase creatinine, accelerate production of insulin-like growth factor, and reduce the blood level of malondialdehyde (MDA) and isoprostane (ISP).

Accordingly, in various aspects, the present technology provides methods comprising administering the compositions described herein daily or at some other frequency to subjects who exhibit any of a variety of physiological diseases or disorders. In various embodiments, methods comprise administering a composition of the present technology to a human or other animal subject in need thereof for addressing the following listed conditions, it being understood, in each instance, such methods of "addressing" include (subject to appropriate regulatory approvals): prevention of the recited disease or disorder; treatment of the recited disease or disorder; amelioration of symptoms associated with the recited disease or disorder, such "amelioration" including avoidance, reduction or elimination of symptoms; reducing or increasing levels of markers or other physiological substances associated with the recited disease or disorder in the blood, urine, or other tissue or product of the subject, so as to improve the associated physiological stated of the subject; reducing the risk of the recited disease or disorder; and promoting health in subjects having the recited disease or disorder.

The present technology provides methods for addressing gene expression (e.g., up-regulating or down-regulating) in a subject, including administering to the person any of the compositions of the present technology, on a one time or periodic basis.

The present technology provides methods for addressing (e.g., treating, preventing, reducing the risk of) disorders associated with oxidative radicals in a subject, including administering to the person any of the compositions of the present technology, on a one time or periodic basis.

The present technology provides methods for addressing (e.g., decreasing) oxidative DNA damage in a subject, comprising administering to the person any of the compositions of the present technology, on a one time or periodic basis.

The present technology provides methods for addressing (e.g., improving) cognitive function in a subject, comprising administering to the person any of the compositions of the present technology, on a one time or periodic basis.

The present technology provides methods for addressing (e.g., treating, preventing, reducing the risk of) pre-diabetes in a subject, comprising administering to the person any of the compositions of the present technology, on a one time or periodic basis.

The present technology provides methods for addressing (e.g., treating, preventing, reducing the risk of) diabetes in a subject, comprising administering to the person any of the compositions of the present technology, on a one time or periodic basis.

The present technology provides methods for addressing (e.g., reducing) blood A1C levels in a subject, comprising administering to the person any of the compositions of the present technology, on a one time or periodic basis.

The present technology provides methods for addressing (e.g., treating, preventing, reducing the risk of) non-alcoholic fatty liver disease in a subject, comprising administering to the person any of the compositions of the present technology, on a one time or periodic basis.

The present technology provides methods for addressing (e.g., treating, preventing, reducing the risk of) non-alcoholic steatohepatitis in a subject, comprising administering to the person any of the compositions of the present technology, on a one time or periodic basis.

The present technology provides methods for addressing (e.g., treating, preventing, reducing the risk of, ameliorating symptoms of) brain injury in a subject, comprising administering to the person any of the compositions of the present technology, on a one time or periodic basis.

The present technology provides methods for addressing cancer (e.g., treating, preventing, reducing the risk of) in a subject, comprising administering to the person any of the compositions of the present technology, on a one time or periodic basis.

The present technology provides methods for addressing (e.g., reducing) blood pressure in a subject, comprising administering to the person any of the compositions of the present technology, on a one time or periodic basis.

The present technology provides methods for addressing (e.g., treating, preventing, reducing the risk of) preeclampsia in a subject, comprising administering to the person any of the compositions of the present technology, on a one time or periodic basis.

The present technology provides methods for addressing (e.g., treating, preventing, reducing the risk of) obesity in a subject, comprising administering to the person any of the compositions of the present technology, on a one time or periodic basis.

The present technology provides methods for addressing (e.g., reducing) blood lipid levels in a subject, comprising administering to the person any of the compositions of the present technology, on a one time or periodic basis.

The present technology provides methods for addressing (e.g., reducing, reducing the risk of high) blood pressure in a subject, comprising administering to the person any of the compositions of the present technology, on a one time or periodic basis.

The present technology provides methods for addressing (e.g, improving, increasing) intestinal flora in a subject, comprising administering to the person any of the compositions of the present technology, on a one time or periodic basis.

The present technology provides methods for addressing (e.g., treating, preventing, reducing the risk of, ameliorating the symptoms of) cerebral apoplexy in a subject, comprising administering to the person any of the compositions of the present technology, on a one time or periodic basis.

The present technology provides methods for addressing (e.g., reducing) blood cholesterol levels in a subject, comprising administering to the person any of the compositions of the present technology, on a one time or periodic basis.

The present technology provides methods for addressing (e.g., improving) renal function in a subject, comprising administering to the person any of the compositions of the present technology, on a one time or periodic basis.

The present technology provides methods for addressing (e.g., decreasing) insulin resistance, in a subject, comprising administering to the person any of the compositions of the present technology, on a one time or periodic basis.

The present technology provides methods for addressing (e.g., treating, preventing, reducing the risk of) gout in a subject, comprising administering to the person any of the compositions of the present technology, on a one time or periodic basis.

The present technology provides methods for addressing (e.g., treating, preventing, reducing the risk of) anxiety in a subject, comprising administering to the person any of the compositions of the present technology, on a one time or periodic basis.

The present technology provides methods for addressing sleep (e.g., improving sleep quality) in a subject, comprising administering to the person any of the compositions of the present technology, on a one time or periodic basis.

The present technology provides methods for addressing (e.g., reducing) pulmonary fibrosis in a subject, comprising administering to the person any of the compositions of the present technology, on a one time or periodic basis.

The present technology provides methods for addressing (e.g., increasing) sperm count in a subject, comprising administering to the person any of the compositions of the present technology, on a one time or periodic basis.

The present technology provides methods for addressing (e.g., treating, preventing, reducing the risk of) inflammatory disorders in a subject, including administering to the person any of the compositions of the present technology, on a one time or periodic basis.

The present technology provides methods for addressing (e.g., decreasing, treating, preventing, reducing the risk of) joint inflammation in a subject, comprising administering to the person any of the compositions of the present technology, on a one time or periodic basis.

The present technology provides methods for addressing (e.g., treating, preventing, reducing the risk of) rheumatoid arthritis in a subject, comprising administering to the person any of the compositions of the present technology, on a one time or periodic basis.

The present technology provides methods for addressing (e.g., treating, preventing, reducing the risk of) osteoarthritis in a subject, comprising administering to the person any of the compositions of the present technology, on a one time or periodic basis.

The present technology provides methods for addressing (e.g., improving) hair health in a subject, comprising administering to the person any of the compositions of the present technology, on a one time or periodic basis.

The present technology provides methods for addressing (e.g., improving) skin health in a subject, comprising administering to the person any of the compositions of the present technology, on a one time or periodic basis.

The present technology provides methods for addressing (e.g., improving) finger and toe nail health in a subject, comprising administering to the person any of the compositions of the present technology, on a one time or periodic basis.

In various embodiments, the methods involve orally administering or providing to the patient with instructions to self-administer the compositions, doses, and formulations that provide a one time or periodic dose of 1 to 12 mg astaxanthin, preferably in the (3S, 3'S) configuration produced by *H. pluvialis*.

Embodiments of the present technology are further illustrated through the following non-limiting examples.

EXAMPLE 1

An astaxanthin daily dose composition contains the following:
  4 mg astaxanthin, (S, S') isomer from *H. pluvialis*; and
  500 mg total omega-3 acids, including 300 mg DHA and 150 mg EPA, from algal oil;
  150 mg phospholipids from sunflower lecithin;
  1.6 mg total omega-6 fatty acids;
  30 mg total omega-5 and omega-7 fatty acids;
  29 mg total omega-9 fatty acids;
  40 mg vitamin E compounds comprising more than 90% by weight of delta-tocotrienol and less than 5% by weight of alpha-tocopherol.

The composition further contains rosemary oil extract, coconut oil, D-limonene, moringa seed oil, pomegranate seed oil, and sea buckthorn pulp oil. The composition contains no beta-carotene, no Coenzyme Q10, no citric acid; and no phosphoric acid.

The composition is provided as two softgels containing 2 mg astaxanthin each, and with instructions to take the 2 softgels daily with food. The composition is used in methods for promoting healthy joints, promoting cardiovascular health, promoting optimal brain functioning, and promoting well-being.

EXAMPLE 2

A male subject, having had diabetes for 18 years, is administered the softgel capsules of the daily dose of Example 1. The subject's blood A1C level decreases from 7.8 to 6.4, and he also reports less arthritis pain.

EXAMPLE 3

A male subject having non-Hodgkins lymphoma, and in renal failure as a side effect of chemo and radiation treatments, is administered the softgel capsules of the daily dose of Example 1 The frequency of his dialysis decreases from once every two weeks to once every three months.

EXAMPLE 4

A male subject having diabetes with A1C as high as 13 is administered 12-24 mg of astaxanthin a day, but still exhibits blood A1C levels in the high 11's and as high as 13. He begins taking softgel capsules of the daily dose of Example 1 and after 6 weeks his blood A1C level is 5.6 with no changes in diet or habits.

EXAMPLE 5

A male subject having a blood triglyceride level of 514 and an LDL level of 102 begins consuming the softgel capsules of the daily dose of Example 1. After 6 weeks, his triglyceride level is 124 and LDL level is 68.

Non-Limiting Listing of Exemplary Embodiments

The present technology includes the following exemplary embodiments.

1. A daily dose of a nutraceutical composition comprising about:
   500 mg total omega-3 acids,
   150 mg phospholipids;
   1.6 mg total omega-6 fatty acids;
   30 mg total omega-5 and omega-7 fatty acids;
   29 mg total omega-9 fatty acids;
   4 mg astaxanthin; and
   40 mg vitamin E compounds comprising more than 90% by weight of delta-tocotrienol and less than 5% by weight of alpha-tocopherol.
2. The dose of Embodiment 1, having no beta-carotene and no Coenzyme Q10.
3. The dose of Embodiment 1, having no citric acid and no phosphoric acid.
4. The dose of Embodiment 1, having essentially no alpha-tocopherol.
5. The dose of Embodiment 1, further comprising one or more of rosemary extract, coconut oil, D-limonene, algal oil, moringa seed oil, Sea Buckthorn pulp oil, and pomegranate seed oil.
6. The dose of Embodiment 1, further comprising rosemary extract, coconut oil, D-limonene, algal oil, moringa seed oil, Sea Buckthorn pulp oil, and pomegranate seed oil.
7. The dose of Embodiment 1, containing no beta-carotene, no Coenyzme Q10, no citric acid, and no phosphoric acid.
8. The dose of any of the above Embodiments, provided in two softgel capsules, wherein each of the two gel capsules comprises half of the daily dose.
9. A formulation comprising about:
   250 mg total omega-3 acids,
   75 mg phospholipids;
   0.8 mg total omega-6 fatty acids;
   15 mg total omega-5 and omega-7 fatty acids;
   14.5 mg total omega-9 fatty acids;
   2 mg astaxanthin; and
   20 mg vitamin E compounds comprising more than 90% by weight of delta-tocotrienol and less than 5% of alpha-tocopherol.
10. The formulation of Embodiment 9, further comprising one or more of rosemary extract, coconut oil, D-limonene, algal oil, moringa seed oil, Sea Buckthorn pulp oil, and pomegranate seed oil.
11. The foimulation of Embodiment 9, further comprising rosemary extract, coconut oil, D-limonene, algal oil, moringa seed oil, Sea Buckthorn pulp oil, and pomegranate seed oil.
12. The formulation of Embodiment 9, containing no beta-carotene, no Coenyzme Q10, no citric acid, and no phosphoric acid.
13. The formulation of Embodiment 9, containing essentially no alpha-tocopherol.
14. A softgel capsule comprising the formulation of Embodiment 9.
15. A daily dose of astaxanthin comprising two of the softgel capsules according to Embodiment 14.
16. A method of reducing A1C in a subject, comprising administering to the patient the daily dose according to Embodiment 1.
17. A method of reducing A1C in a subject, comprising administering to the patient the daily dose according to Embodiment 1.
18. A method of improving renal function in a subject, comprising administering to the patient the daily dose according to Embodiment 1.
19. A method of improving renal function in a subject, comprising administering to the patient the daily dose according to Embodiment 1.
20. A method of improving cognitive function in a subject, comprising administering to the patient the daily dose according to Embodiment 1.
21. A method of improving cognitive function in a subject, comprising administering to the patient the daily dose according to Embodiment 1.
22. A dietary supplement composition comprising astaxanthin, omega-3 fatty acids, phospholipids comprising a major amount of phosphatidyl choline and phosphatidyl inositol, and vitamin E comprising a major amount of delta-tocotrienol.
23. The composition of Embodiment 22, comprising 1-5 mg astaxanthin, 150-500 mg of omega-3 fatty acids, 10-40 mg delta-tocotrienol, and 30-150 mg phospholipids from sunflower lecithin.
24. The composition of Embodiment 22, comprising no coenzyme Q10.
25. The composition of Embodiment 22, comprising no beta-carotene.
26. The composition of Embodiment 22, comprising no citric acid.
27. The composition of Embodiment 22 comprising no phosphoric acid.
28. The composition of Embodiment 22, comprising no coenzyme Q10, no beta-carotene, no citric acid, and no phosphoric acid.
29. The composition of Embodiment 23, comprising no coenzyme Q10, no beta-carotene, no citric acid, and no phosphoric acid.
30. The composition of Embodiment 22, wherein the vitamin E comprises at least 90% by weight delta-tocotrienol and less than 5% by weight alpha-tocopherol.
31. The composition of Embodiment 22, wherein the astaxanthin is from *Haemotococcus pluvialis* algae, the omega-3 fatty acids are from algal oil and comprise a major amount of docosahexaenoic acid and eicosapentaenoic acid, the phospholipids are from sunflower lecithin, and the vitamin E is from annatto.
32. The composition of Embodiment 22, further comprising one or more of rosemary extract, coconut oil, D-limonene, moringa seed oil, Sea Buckthorn pulp oil, and pomegranate seed oil.
33. The composition of Embodiment 22, further comprising rosemary extract, coconut oil, D-limonene, algal oil, moringa seed oil, Sea Buckthorn pulp oil, and pomegranate seed oil.
34. A softgel tablet comprising the composition of any of the preceding Embodiments.
35. A method of reducing A1C in a subject, comprising administering to the subject a dose comprising one or two of the softgel tablets according to Embodiment 34.
36. A method of reducing A1C in a subject, comprising administering to the subject a dose comprising one or two of the softgel tablets according to Embodiment 34.

37. A method of improving renal function in a subject, comprising administering to the subject a dose comprising one or two of the softgel tablets according to Embodiment 34.
38. A method of improving renal function in a subject, comprising administering to the subject a dose comprising one or two of the softgel tablets according to Embodiment 34.
39. A method of improving cognitive function in a subject, comprising administering to the subject a dose comprising one or two of the softgel tablets according to Embodiment 34.
40. A method of improving cognitive function in a subject, comprising administering to the subject a dose comprising one or two of the softgel tablets according to Embodiment 34.
41. A food or beverage comprising astaxanthin, omega-3 fatty acids, phospholipids, and a vitamin E component, wherein the vitamin E component comprises 90% or more by weight of delta-tocotrienol.
42. The food or beverage of Embodiment 41, comprising no coenzyme Q10, no beta-carotene, no citric acid, and no phosphoric acid.

Non-limiting Discussion of Terminology

The foregoing description is merely illustrative in nature and is in no way intended to limit the technology, its application, or uses. The broad teachings of the technology can be implemented in a variety of forms. Therefore, while this technology includes particular examples, the true scope of the technology should not be so limited since other modifications will become apparent upon a study of the drawings, the specification, and the following claims.

The headings (such as "Background" and "Summary") and sub-headings used herein are intended only for general organization of topics within the present technology, and are not intended to limit the technology of the technology or any aspect thereof. In particular, subject matter disclosed in the "Background" may include novel technology and may not constitute a recitation of prior art. Subject matter disclosed in the "Summary" is not an exhaustive or complete technology of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

It should be understood that one or more steps within a method may be executed in different order (or concurrently) without altering the principles of the present technology. Further, although each of the embodiments is described above as having certain features, any one or more of those features described with respect to any embodiment of the technology can be implemented in and/or combined with features of any of the other embodiments, even if that combination is not explicitly described. In other words, the described embodiments are not mutually exclusive, and permutations of one or more embodiments with one another remain within the scope of this technology. For example, a component which may be A, B, C, D or E, or combinations thereof, may also be defined, in some embodiments, to be A, B, C, or combinations thereof.

As used herein, the phrase at least one of A, B, and C should be construed to mean a logical (A OR B OR C), using a non-exclusive logical OR, and should not be construed to mean "at least one of A, at least one of B, and at least one of C."

As used herein, the words "prefer" or "preferable" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein. Further, as used herein the term "consisting essentially of" recited materials or components envisions embodiments "consisting of" the recited materials or components.

"A" and "an" as used herein indicate "at least one" of the item is present; a plurality of such items may be present, when possible.

Unless specified otherwise, all percentages herein are by weight.

Numeric values stated herein should be understood to be approximate, and interpreted to be about the stated value, whether or not the value is modified using the word "about." Thus, for example, a statement that a parameter may have value "of X" should be interpreted to mean that the parameter may have a value of "about X." The term "about" indicates that the calculation or the measurement allows some slight imprecision in the value (with some approach to exactness in the value; approximately or reasonably close to the value; nearly). One of ordinary skill in the art will appreciate that any such recited value is subject to variance due to, for example, imprecision in measurement techniques, and variation in naturally-occurring materials, and variation in synthetic or manufacturing processes. Accordingly, if, for some reason, the imprecision provided by "about" is not otherwise understood in the art with this ordinary meaning, then "about" as used herein indicates variations that may arise from ordinary methods of manufacturing, measuring or using the material, device or other object to which the calculation or measurement applies.

As referred to herein, ranges are, unless specified otherwise, inclusive of endpoints and include disclosure of all distinct values and further divided ranges within the entire range. Thus, for example, a range of "from A to B" is inclusive of A and of B. Further, the phrase "from A to B" includes variations in the values of A and B, which may be slightly less than A and slightly greater than B; the phrase may be read be "about A, from A to B, and about B." Disclosure of values and ranges of values for specific parameters (such as temperatures, molecular weights, weight percentages, etc.) are not exclusive of other values and ranges of values useful herein.

It is also envisioned that two or more specific exemplified values for a given parameter may define endpoints for a range of values that may be claimed for the parameter. For example, if Parameter X is exemplified herein to have value A and is also exemplified to have value Z, it is envisioned that Parameter X may have a range of values from about A to about Z. Similarly, it is envisioned that disclosure of two or more ranges of values for a parameter (whether such ranges are nested, overlapping or distinct) subsumes all possible combination of ranges for the value that might be embodied in the present technology (i.e., claimed) using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

Further, as referred to herein, numeric ranges recited as "greater than" or "less than" a recited value are inclusive of the recited value, and interpreted to mean "about or greater than" the recited value or "about or less than" the recited value, respectively.

What is claimed is:

1. A synergistic unit dose composition comprising:
   from 1 mg to 5 mg of astaxanthin;
   from 200 mg to 300 mg of omega-3 acids,
   from 70 mg to 80 mg of phospholipids; and
   from 15 mg to 25 mg of vitamin E compounds, the vitamin E compounds comprising more than 90% by weight of delta-tocotrienol and less than 5% of alpha-tocopherol.

2. The composition of claim 1, further comprising:
   from 0.5 mg to 1 mg of total omega-6 fatty acids;
   from 10 mg to 20 mg of an admixture comprising omega-5 and omega-7 fatty acids; and
   from 12 mg to 16 mg of total omega-9 fatty acids.

3. The composition of claim 2, further comprising one or more of rosemary extract, coconut oil, D-limonene, algal oil, moringa seed oil, Sea Buckthorn pulp oil, and pomegranate seed oil.

4. The composition of claim 1, wherein the omega-3 acids comprise DHA and EPA.

5. The composition of claim 1, wherein the phospholipid is lecithin.

6. The composition of claim 1, wherein the astaxanthin is from *Haemotococcus pluvialis* algae, the omega-3 fatty acids are from algal oil and comprise a major amount of docosahexaenoic acid and eicosapentaenoic acid, the phospholipids are from sunflower lecithin, and the vitamin E is from annatto.

7. The composition of claim 2, wherein the composition does not contain beta-carotene, lutein, zeaxanthin, echinenone, canthaxanthin, or coenzyme Q10 or phosphoric acid.

8. A synergistic unit dose composition consisting of:
   from 1 mg to 5 mg of astaxanthin;
   from 200 mg to 300 mg of omega-3 acids, the omega-3 acids comprising from ®mg to 400 mg of DHA and from 100 mg to 200 mg of EPA;
   from 70 mg to 80 mg of lecithin;
   from 15 mg to 25 mg of vitamin E compounds, the vitamin E compounds comprising more than 90% by weight of delta-tocotrienol and less than 5% of alpha-tocopherol;
   from 0.5 mg to 1 mg of omega-6 fatty acids;
   from 10 mg to 20 mg of an admixture comprising omega-5 and omega-7 fatty acids;
   from 12 mg to 16 mg of omega-9 fatty acids; and
   optionally, one or more of rosemary extract, coconut oil, D-limonene, algal oil, moringa seed oil, Sea Buckthorn pulp oil, and pomegranate seed oil.

9. The composition of claim 8, wherein the astaxanthin is from *Haemotococcus pluvialis* algae, the omega-3 fatty acids are from algal oil and comprise a major amount of docosahexaenoic acid and eicosapentaenoic acid, the lecithin is from sunflowers, and the vitamin E is from annatto.

10. A method of improving the nutritional status of a human or other animal subject, comprising administering to the subject, one or more times per day, a synergistic composition comprising, nutritional materials comprising:
    from 2 mg to 6 mg of astaxanthin;
    from 400 mg to 600 mg of omega-3 acids;
    from 100 mg to 200 mg of phospholipids; and
    from 35 mg to 45 mg of vitamin E compounds, the vitamin E compounds comprising more than 90% by weight of delta-tocotrienol and less than 5% by weight of alpha-tocopherol.

11. The method of claim 10, wherein the nutritional materials further comprise:
    from 1 mg to 3 mg of omega-6 fatty acids;
    from 25 mg to 35 mg of an admixture comprising omega-5 and omega-7 fatty acids; and
    from 35 mg to 45 mg of total omega-9 fatty acids.

12. The method of claim 10, wherein the nutritional materials further comprise one or more of rosemary extract, coconut oil, D-limonene, algal oil, moringa seed oil, Sea Buckthorn pulp oil, and pomegranate seed oil.

13. The method of claim 10, wherein the omega-3 acids comprise from 200 mg to 400 mg of DHA and from 100 mg to 200 mg of EPA, and the phospholipid is lecithin.

14. The method of claim 10, wherein the astaxanthin is from *Haemotococcus pluvialis* algae, the omega-3 fatty acids are from algal oil and comprise a major amount of docosahexaenoic acid and eicosapentaenoic acid, the phospholipid is lecithin from sunflowers, and the vitamin E is from annatto.

15. The method of claim 10, wherein the nutritional materials do not contain beta-carotene, lutein, zeaxanthin, echinenone, canthaxanthin, coenzyme Q10, or phosphoric acid.

16. The method of claim 10, wherein the administering comprises ingestion by the subject of two unit dosage forms comprising the nutritional materials.

17. The method of claim 10, for reducing blood A1C levels in the subject.

18. The method of claim 10, wherein the subject has reduced renal function.

19. The method of claim 10, for improving cognitive function in the subject.

20. The composition of claim 1, wherein the delta-tocotrienol is annatto derived delta-tocotrienol.

\* \* \* \* \*